United States Patent [19]
Taguchi et al.

[11] Patent Number: 5,401,770
[45] Date of Patent: Mar. 28, 1995

[54] ANTIPRURITIC AGENTS AND ANTIPRURITIC COMPOSITIONS THEREOF

[75] Inventors: Shigeru Taguchi; Miwako Inokuchi; Noriko Nakajima; Mie Inomata; Yasuo Naito, all of Yokohama, Japan

[73] Assignee: Shiseido Company Ltd., Tokyo, Japan

[21] Appl. No.: 917,015

[22] PCT Filed: Dec. 11, 1991

[86] PCT No.: PCT/JP91/01703

§ 371 Date: Aug. 11, 1992

§ 102(e) Date: Aug. 11, 1992

[87] PCT Pub. No.: WO92/10178

PCT Pub. Date: Jun. 25, 1992

[30] Foreign Application Priority Data

Dec. 11, 1990 [JP] Japan .................................. 2-415763

[51] Int. Cl.$^6$ ...................... C07C 3/06; A61K 31/315
[52] U.S. Cl. .................................. 514/494; 514/186; 548/104; 556/133
[58] Field of Search ................ 548/495, 104; 556/133; 514/186, 494

[56] References Cited

U.S. PATENT DOCUMENTS

| | | | |
|---|---|---|---|
| 4,053,630 | 10/1977 | Yu et al. | 424/289 |
| 4,089,954 | 5/1978 | Morelle et al. | 514/184 |
| 4,112,954 | 11/1978 | Morelle et al. | 514/184 |
| 4,652,445 | 3/1987 | Ort | 424/70 |
| 4,711,780 | 12/1987 | Fahim | 424/145 |
| 4,937,234 | 6/1990 | Fahim | 514/564 |
| 5,166,149 | 11/1992 | Loev | 514/186 |

FOREIGN PATENT DOCUMENTS

| | | |
|---|---|---|
| 0059882 | 9/1982 | European Pat. Off. . |
| 0139480 | 2/1985 | European Pat. Off. . |
| 0245669 | 11/1987 | European Pat. Off. . |
| 2550446 | 11/1987 | France . |
| WO9015603 | 12/1990 | WIPO . |
| WO9213518 | 8/1992 | WIPO . |

*Primary Examiner*—David B. Springer
*Attorney, Agent, or Firm*—Foley & Lardner

[57] ABSTRACT

An antipruritic agent comprising a zinc-amino acid complex, and an antipruritic composition containing said antipruritic agent at a concentration of $2.6 \times 10^{-3}$ to $2.6 \times 10^{-1}$ M.

9 Claims, No Drawings

ANTIPRURITIC AGENTS AND ANTIPRURITIC COMPOSITIONS THEREOF

TECHNICAL FIELD

The present invention relates to an antipruritic agent and an antipruritic compound, and more specifically, it relates to an antipruritic agent and an antipruritic compound, in which zinc is the main ingredient.

BACKGROUND ART

The skin possesses the function of protecting the body from various forms of stress due to the external environment, but if this body maintenance function becomes unbalanced, various forms of skin conditions appear, such as chapped skin and scabies.

As the majority of these skin conditions are accompanied by itching, this itching leads to skin pruritis, which can frequently exacerbate the original skin condition.

There are individual differences in the degree of itching in such cases of pruritic skin diseases and cases of skin pruritis, ranging from that which is extremely mild to that which is extremely severe. In addition, as a sebum deficiency, which is one cause of pruritis, is observed to some degree in the case of elderly subjects, there are cases in which urea ointment and zinc oxide ointment, etc. are used because of the moisture effects thereof.

Moreover, steroid preparations, anti-histamines and Crotamiton preparations, etc., have been widely used in the past as antipruritics.

Nevertheless, itching accompanying liver and renal disfunction and malignant tumors, metabolic disorders and senile pruritis, and pruritic skin diseases such as atopic dermatitis, eczema and urticaria, against which these antipruritics are unable to demonstrate antipruritic effects, are becoming a serious problem in the clinical setting.

As these diseases are frequently accompanied by serious itching, the particular condition may be exacerbated due to scratch to the skin resulting from that itching. As such, an antipruritic able to demonstrate adequate antipruritic effects has been long awaited. Furthermore, steroid preparations, antihistamines, and so on may cause problems due to adverse side effects, in certain cases.

DISCLOSURE OF THE INVENTION

Accordingly, the object of the present is to eliminate the above-mentioned problems of the prior art by providing an antipruritic agent and antipruritic compound free of adverse side effects, acting directly on the itching itself, and being fast-acting.

In accordance with the present invention, there is provided an antipruritic comprising a zinc-amino acid complex.

In accordance with the present invention, there is also provided an antipruritic compound comprising an antipruritic agent comprised of a zinc-amino acid complex at a concentration of $2.6 \times 10^{-3} - 2.6 \times 10^{-1}$M (molar concentration, moles/liter), and a pharmacologically acceptable carrier.

BEST MODE OF CARRYING OUT THE INVENTION

As a result of intensive research by the inventors of the present invention, to achieve the above-mentioned object, it was discovered that an antipruritic agent having superior antipruritic properties and superior useability could be obtained by bonding zinc and an amino acid in a specific proportion, which led to the completion of the present invention.

Thus, it has been reported that itching receptors exist between the epidermis and dermis layers of the skin ("Modern Medicine", Vol. 16, No. 11, pp. 46-47, 1987, Asahi Shimbunsha), and that the skin contains a high content of zinc, containing roughly 20% of the total amount of zinc in the body, with particularly large amounts contained in the epidermis ("Zinc and Clinical Medicine", Asakura Shoten, pp. 20-21, p. 123, 1984), indicating that there is an intimate relationship between the skin and zinc metabolism. In addition, a characteristic systemic skin rash occurs in hereditary Acrodermatitis entheropathica, which is primarily caused by zinc deficiency, and a long-term implementation of high-calorie infusions (venous feeding). The cause of this in the former case is an insufficient absorption of zinc in the small intestine, while the cause in the latter case is the chelation of zinc in the body by amino acids and sugars contained in the infusion liquid resulting in transport and excretion of zinc outside the body. It has also been reported that these skin diseases are recovered by a replacement of zinc ("Zinc and Clinical Medicine", Asakura Shoten, pp. 77-97, 1984). The inventors of the present invention thus conducted their research by focusing on the relationship between zinc and itching. As amino acids and sugars were considered for use as carriers of zinc based on the results of research into zinc metabolism, a bound form of zinc and amino acid was used for the form in which zinc is supplied to the body.

The following provides a detailed description of the constitution of the present invention.

The zinc and amino acid, the main ingredients, are known substances and may be those which are commercially available.

The supply form of the zinc used in the present invention refers to zinc metal, its inorganic salts such as a sulfate, carbonate or nitrate thereof, as well as its organic salts such as an acetate or oxalate thereof.

In addition, the amino acid referred to in the present invention refers to neutral, acidic and basic and all other amino acids as well as their inorganic salts such as hydrochlorides thereof and their organic salts such as acetates thereof. Furthermore, neutral to acidic amino acids are particularly preferable, as they enhance the antipruritic effects.

In the antipruritic agent of the present invention, the preferable bonding mole ratio of zinc to amino acid is 1:2. When the bonding procedure is performed at a mole ratio of less than 1:2, adequate effects corresponding to the amount of zinc will not be obtained. In addition, when the amino acid is blended in at a mole ratio in excess of 1:2, no effects will be demonstrated due to the excess amount of amino acid.

The amount of zinc-amino acid complex blended into the antipruritic composition of the present invention is generally $2.6 \times 10^{-3} - 2.6 \times 10^{-1}$M, preferably $1.3 \times 10^{-2} - 2 - 1.3 \times 10^{-1}$M. When the amount of zinc-amino acid complex blended is too low, although the manufacturing of the drug is easy, the antipruritic effects are inferior, thus making this undesirable. Conversely, when the amount of zinc-amino acid complex blended is too high, it is necessary to use a large amount of glycerine and alcohol to dissolve the zinc-amino acid complex. This lowers the stability of the preparation and hinders the useability thereof, thus making this undesirable.

Furthermore, where the zinc-amino acid complex is less than $1.3 \times 10^{-1}$M, since it is soluble in water and physiological saline, it can be dissolved as is, thus allowing it to be used for external application or as an injection drug. Where, however, the zinc-amino acid complex exceeds $13 \times 10^{-1}$M, since it cannot be dissolved in water as is, it must be dissolved in glycerine, ethyl alcohol, glycol or water, etc.

The amount blended when blending glycerol into the antipruritic composition pertaining to the present invention is generally 5.0–60.0 wt %, preferably 10.0–50.0 wt %.

When the amount of glycerine blended is too low, it is not possible to dissolve the zinc-amino acid complex, thus making this undesirable. Conversely, when the amount of glycerine is too high, the useability of the composition is remarkably hindered, thus also making this undesirable.

A poly-glycerol such as di-glycerol can be used alone or in combination with glycerol, to dissolve the zinc-amino acid complex in place of glycerol.

The blended amount when blending ethyl alcohol into the antipruritic composition pertaining to the present invention is 3.0–50.0 wt %, preferably 5.0–40.0 wt %.

When the amount of ethyl alcohol blended is too low, it is not possible to dissolve the zinc, etc., thus making this undesirable.

Conversely, when the amount blended is too high, there is an increase in the degree of skin irritation, thus also making this undesirable.

Isopropyl alcohol or acetone, etc., also can be used to dissolve the zinc, etc., in place of ethyl alcohol, but ethyl alcohol is preferable in terms of solubility.

Examples of the glycol blended into the antipruritic composition pertaining to the present invention include propylene glycol, dipropylene glycol, 1,3-butylene glycol, hexylene glycol and polyethylene glycol. These glycols are blended in to function as assistants in dissolving the zinc-amino acid complex, and the amount blended is 0.5–30.0 wt %, preferably 5.0–20.0 wt %.

When the amount of glycol blended is too low, a large amount of glycerol and ethyl alcohol must be blended in order to dissolve the zinc-amino acid complex, and conversely, when the amount blended is too high, it will not be possible to dissolve the zinc-amino acid complex, thus making both cases undesirable.

In addition, the amount of water blended into the antipruritic compound pertaining to the present invention is generally 5.0–50.0 wt %, preferably 10.0–40.0 wt %.

As the zinc-amino acid complex most likely exists in the form of a complex, its solubility is extremely specific, and its stability is greatly affected by the pH thereof.

The antipruritic composition according to the present invention is maintained stable for a long time by adjusting same to a pH of 2.0–10.0, preferably 4.0–8.0.

In order to prepare an antipruritic composition in accordance with the present invention, antioxidants, preservatives, buffers, polar oils, surface activators, water-soluble polymers and other drugs can be blended as desired, in addition to the above-mentioned required ingredients.

Furthermore, as previously described, although glycerol, ethyl alcohol, glycol and water are required to dissolve a zinc-amino acid complex, etc., in excess of $1.3 \times 10^{-1}$M, where the amount of zinc-amino acid complex is less than $1.3 \times 10^{-1}$M, a combination of the abovementioned ingredients is not always necessary.

In addition, the present invention is able to be applied in pharmaceutical or non-pharmaceutical products, as well as in cosmetics and drinks, and so on.

When using the antipruritic agent according to the present invention as a antipruritic composition for external application on the skin, the amount of zinc-amino acid complex is generally made to be $2.6 \times 10^{-3} - 2.6 \times 10^{-1}$M, preferably $1.3 \times 10^{-2} - 1.3 \times 10^{-1}$M.

Furthermore, when using the external use composition according to the present invention as a preparation for external application on the skin, those ingredients that are normally blended into ordinary external preparations for application on the skin, such as oils, water, surface activators, moisture retention agents, lower alcohols, thickeners, chelating agents, dyes, preservatives and perfumes, may be suitably blended.

In addition, external preparations for application on the skin broadly refer to those preparations used on the skin, and examples include external use medications such as ointments as well as facial cosmetic products such as a skin wash, milky lotions and cremes.

Moreover, the external use composition according to the present invention also can be used on the head. Examples of these applications include hair tonic, milky lotions for the scalp, hair liquid, hair shampoo, hair rinse, hair cream, and hair spray.

When used as a composition for external use on the head, oily ingredients, UV absorbers, preservatives, moisture retention agents, surface activators, perfumes, water, alcohol, thickeners, coloring agents, medicinal drugs, and so on can be blended in.

When using the antipruritic agent according to the present invention as an internal medicine or injection, those ingredients which are normally blended in general internal medicines and injections can be suitably blended in as necessary. Examples of such ingredients include vehicles such as cornstarch, lactose, glucose and crystal cellulose; binders such as starch, gelatin and acacia; decomposing agents such as agar, sodium carboxycellulose and sodium hydrogencarbonate; lubricating agents such as magnesium stearate and talc,; isotonic agents such as sodium chloride; buffers such as phosphate and borate; and, other additives, dissolving assistants, stabilizers and preservatives.

In addition, examples of the forms of these internal medicines include pharmaceuticals as well as powders, grains, granules, pills, tablets, capsules, internally consumed liquids and drinks in health foods, and beverages and so on.

EXAMPLES

The following provides an explanation of suitable Examples of the present invention, but it is understood that the present invention is not limited to these Examples. Furthermore, unless specified otherwise, the zinc and amino acid amounts are indicated in molar concentrations.

First, the manufacturing process of the antipruritic agent according to the present invention will be explained.

Example 1

Zinc-Glycine Complex (H$_2$N—CH$_2$—COO)$_2$Zn

While stirring at 60° C. after dissolving 1.65 g of glycine (commercially available product) in water, a solution of 2.37 g of zinc acetate dihydrate dissolved in 6 ml of water was dropwise added thereto. Stirring was performed for 30 minutes at the same temperature, after which the solution was allowed to stand overnight in a refrigerator. The precipitated solid was recovered by filtration and recrystallized with a mixture of ethanol and water to obtain 3.52 g of crystal.

M.P.: >270° C.
IR$_{(KBr)}$: 3350, 1640 cm$^{-1}$
Elementary analysis values: C$_4$H$_8$N$_2$O$_4$Zn.H$_2$O
Calculated values: C 8.97, H 1.88, N 5.23
Analytical values: C 8.88, H 1.75, N 5.18

Example 2

Zinc-Aspartic Acid Complex

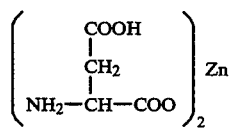

L-aspartic acid (2.00 g, 15.0 mmol) was added to an MeOH solution of NaOMe (prepared with Na: 0.69 g, MeOH: 50 ml) at 0° C. and stirred. An MeOH solution (30 ml) of zinc acetate dihydrate (3.30 g) was then gradually dropwise added thereto at room temperature. After stirring for 2 hours at that same temperature, the precipitated crystal (in suspension) was recovered by filtration, washed with water, air dried, and then dried under a reduced pressure (5 mmHg, 80° C.).

Yield: 1.65 g
M.P.: >270° C.
IR$_{(KBr)}$: 3300, 1640, 1630 cm$^{-1}$
Elementary analysis values: C$_8$H$_{12}$N$_2$O$_8$Zn.H$_2$O
Calculated values: C 27.64, H 4.06, N 8.06
Analytical values: C 27.88, H 4.10, N 7.90

Example 3

Zinc-Glutamic Acid Complex

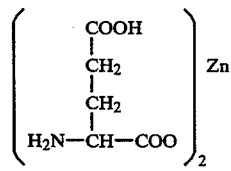

L-glutamic acid (2.0 g, 13.6 mmol) was added to an MeOH solution of NaOMe (prepared with Na: 0.31 g, MeOH: 50 ml) at 0° C. and stirred. An MeOH solution (30 ml) of zinc acetate dihydrate (1.49 g) was then slowly dropwise added thereto. After refluxing and stirring for 5 hours, the precipitated crystal (in suspension) was recovered by filtration, washed with water, air dried, and then dried under a reduced pressure (5 mmHg, 80° C.).

Yield: 1.40 g
M.P.: >270° C.
IRr$_{(KBr)}$: 3400, 1645, 1640 cm$^{-1}$
Elementary analysis values: C$_{10}$H$_6$N$_{2n}$O$_8$Zn.2H$_2$O
Calculated values: C 30.51, H 5.12, N 7.12
Analytical values: C 30.79, H 4.92, N 7.35

Example 4

Zinc-Valine Complex

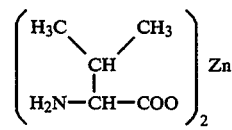

L-valine (2.00 g, 17.1 mmol) was added to an MeOH solution of NaOMe (prepared with Na: 0.39 g, MeOH: 50 ml) at 0° C. and stirred. An MeOH solution (30 ml) of zinc acetate dihydrate (1.90 g) was then slowly dropwise added thereto at room temperature. After stirring for 6 hours at that same temperature, the precipitated crystal (in suspension) recovered by filtration, washed with water, air dried, and then dried under a reduced pressure (5 mmHg, 80° C.).

Yield: 0.40 g
M.P.: >270° C.
IR$_{(KBr)}$: 3400, 1640 cm$^{-1}$
Elementary analysis values: C$_{10}$H$_{20}$N$_2$O$_4$Zn.3/2H$_2$O
Calculated values: C 36.99, H 7.14, N 8.68
Analytical values: C 37.13, H 6.92, N 8.46

Example 5

Zinc-Isoleucine Complex

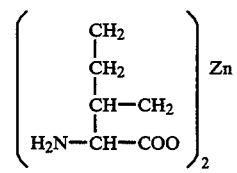

L-isoleucine (2.00 g, 15.3 mmol) was added to an MeOH solution of NaOMe (prepared with Na: 0.35 g, MeOH: 50 ml) at 0° C. and stirred. An MeOH solution (30 ml) of zinc acetate dihydrate (1.67 g) was then slowly dropwise added thereto at room temperature. After stirring for hours at the same temperature, the solution was concentrated to half its original volume, followed by the addition of an equal volume of water. The precipitated crystal was recovered by filtration, air dried, and then dried under a reduced pressure (5 mmHg, 80° C.).

Yield: 1.03 g
M.P.: >270° C.
IR$_{(KBr)}$: 3350, 1635 cm$^{-1}$
Elementary analysis values: C$_{12}$H$_{24}$N$_2$O$_4$Zn.½H$_2$O
Calculated values: C 43.06, H 7.53, N 8.37
Analytical values: C 43.15, H 7.42, N 8.36

Example 6

Zinc-Histidine Complex

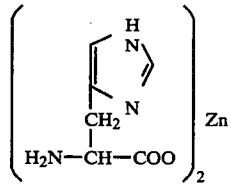

L-histidine (2.00 g, 12.8 mmol) was added to an MeOH solution of NaOMe (prepared with Na: 0.30 g, MeOH: 50 ml) at 0° C. and stirred. An MeOH solution (30 ml) of zinc acetate dihydrate (1.41 g) was then slowly dropwise added thereto at room temperature. After stirring for 3 hours, the precipitated crystal (in suspension) was recovered by filtration, washed with water, air dried, and then concentrated under a reduced pressure (5 mmHg, 80° C.).

Yield: 0.40 g
M.P.: >285° C.
IR$_{(KBr)}$: 3310, 1640 cm$^{-1}$
Elementary analysis values: $C_{12}H_{16}N_6O_4Zn.3/2H_2O$
Calculated values: C 35.97, H 4.78, N 20.97
Analytical values: C 36.21, H 4.58, N 20.75

Example 7

Zinc-Phenylalanine Complex

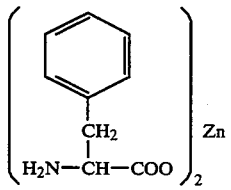

L-phenylalanine (2.00 g, 12.1 mmol) was added to an MeOH solution of NaOMe (prepared with Na: 0.30 g, MeOH: 50 ml) at 0° C. and stirred. An MeOH solution (30 ml) of zinc acetate dihydrate (1.30 g) was then slowly dropwise added thereto at room temperature. After stirring for 3 hours, the precipitated crystal (in suspension) was recovered by filtration, washed with water, air dried, and then dried under a reduced pressure (5 mmHg, 80° C.).

Yield: 2.06 g
M.P.: >270° C.
IR$_{(KBr)}$: 3300, 1640 cm$^{-1}$
Elementary analysis values: $C_{18}H_{20}N_2O_4Zn.H_2O$
Calculated values: C 54.91, H 5.12, N 7.11
Analytical values: C 54.73, H 5.13, N 7.00

Example 8

Zinc-Methionine Complex

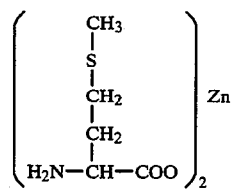

L-methionine (2.00 g, 13.4 mmol) was added to an MeOH solution of NaOMe (prepared with Na: 0.30 g, MeOH: 50 ml) at 0° C. and stirred. An MeOH solution (30 ml) of zinc acetate dihydrate (1.50 g) was then slowly dropwise added thereto at room temperature. After stirring for 3 hours, the precipitated crystal (in suspension) was recovered by filtration, washed with water, air dried, and then dried under a reduced pressure (5 mmHg, 80° C.).

Yield: 2.13 g
M.P.: >270° C.
IR$_{(KBr)}$: 3310, 1640 cm$^{-1}$
Elementary analysis values: $C_{18}H_{20}N_2O_4Zn.3/2H_2O$
Calculated values: C 33.20, H 5.57, N 7.74
Analytical values: C 33.12, H 5.70, N 7.66

Example 9

Zinc-Leucine Complex

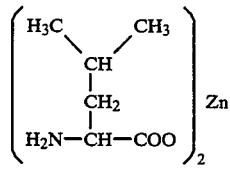

L-Leucine (2.00 g, 15.3 mmol) was added to an MeOH solution of NaOMe (prepared with Na: 0.36 g, MeOH: 50 ml) at 0° C. and stirred. An MeOH solution (30 ml) of zinc acetate dihydrate (1.67 g) was then slowly dropwise added thereto at room temperature. After stirring for 2 hours at that same temperature, the solution was concentrated to half its original volume, followed by the addition of an equal volume of water. The precipitated crystal was recovered by filtration, air dried, and then dried under a reduced pressure (5 mmHg, 80° C.).

Yield: 2.00 g
M.P.: >270° C.
IR$_{(KBr)}$: 3350, 1635 cm$^{-1}$
Elementary analysis values: $C_{12}H_{24}N_2O_4Zn.\frac{1}{2}H_2O$
Calculated values: C 43.06, H 7.53, N 8.37
Analytical values: C 43.29, H 7.34, N 8.29

The antipruritic effects of the zinc-amino acid complex according to the present invention were examined as follows.

Antipruritic Effects Test

Although the primary cause of itching is believed to be mainly related to histamine, there are many cases of itching which cannot be suppressed with anti-histamines, and these cases create serious problems in the clinical setting.

As such, prurigenic animal models were prepared in which itching cannot be suppressed by anti-histamines, by intracutaneously administering either bradykinin or kallikrein to guinea pigs, in order to confirm the antipruritic effects of the antipruritic agent according to the present invention.

(1) Antipruritic Effects Against Itching Induced by Bradykinin in Prurigenic Animals The prurigenic substance, bradykinin, was intracutaneously administered to the flanks of healthy Hartley male guinea pigs to obtain the prurigenic animals.

The itching behavior was then evaluated following the evaluation standards indicated below, expressed in the form of itching activity.

| Evaluation Method | Score |
| --- | --- |
| (1) Stressful behavior due to itching<br>When the animal demonstrated the following forms of behavior not normally observed:<br>*Scratching of the face, ears, etc., with forepaw<br>*Trembling of the body<br>*Biting the floor or paws<br>*Firmly standing on back legs | 1 |
| (2) Scratching of the prurigenic site on the flank with the mouth or back legs | 2 |
| (3) Continuously repeating the behavior of (2) above three or more times | 3 |

The above behavioral observations were performed simultaneously by three subjects or more for 20 minutes for each group of animals. The itching activity was scored and the mean value was then determined. These mean values were then indicated as antipruritic effects, taking the itching activity of a vehicle control group to be 100%.

The hair of the right flanks of healthy male guinea pigs (body weight: 450–600 g) was shaven using an electric shaver on the previous day, and thereafter the animals were grouped into groups of five animals each. Each of the groups were intracutaneously administered with 50 μg/0.05 ml of bradykinin into the right flank. After five minutes had elapsed, an externally applied vehicle was applied to one of the groups (control group)(composition: glycerine 40%, ethanol 25%, and water 35%). For the other groups, 0.1 ml of each sample containing the test substance at each concentration was externally applied to the site of intracutaneous administration of bradykinin. The itching behavior was then observed for 20 minutes, to determine the itching activity score.

A study was thus conducted regarding the type of amino acid and antipruritic effects based on the evaluation method described above. The results are indicated in Table 1.

TABLE 1

Relationship Between Amino Acid and Itching Activity (n = 5)

| Amino Acid | Conc. | Zinc | Conc. | Itching Activity (%) |
| --- | --- | --- | --- | --- |
| Vehicle control | — | — | — | 100.0 |
| Glycine | $2 \times 10^{-2}$ M | Zinc sulfate | $1 \times 10^{-2}$ M | 67.5 |
| Serine | $2 \times 10^{-2}$ M | Zinc sulfate | $1 \times 10^{-2}$ M | 73.0 |
| Cysteine | $2 \times 10^{-2}$ M | Zinc sulfate | $1 \times 10^{-2}$ M | 70.8 |
| Leucine | $2 \times 10^{-2}$ M | Zinc sulfate | $1 \times 10^{-2}$ M | 82.3 |
| Methionine | $2 \times 10^{-2}$ M | Zinc sulfate | $1 \times 10^{-2}$ M | 70.5 |
| Tyrosine | $2 \times 10^{-2}$ M | Zinc sulfate | $1 \times 10^{-2}$ M | 70.5 |
| Tryptophan | $2 \times 10^{-2}$ M | Zinc sulfate | $1 \times 10^{-2}$ M | 72.6 |
| Glutamic acid | $2 \times 10^{-2}$ M | Zinc sulfate | $1 \times 10^{-2}$ M | 62.9 |
| Histidine | $2 \times 10^{-2}$ M | Zinc sulfate | $1 \times 10^{-2}$ M | 90.0 |
| Arginine | $2 \times 10^{-2}$ M | Zinc sulfate | $1 \times 10^{-2}$ M | 93.4 |
| Lysine | $2 \times 10^{-2}$ M | Zinc sulfate | $1 \times 10^{-2}$ M | 94.3 |

As is clear from Table 1, although a decrease in itching activity is observed for all zinc-amino acid complexes, particularly favorable antipruritic effects are observed for complexes of zinc and neutral to acidic amino acids.

The relationship between the bonding ratio of the zinc-amino acid complex and itching activity was examined as follows.

More specifically, the itching activity was examined by sequentially varying the amount of amino acid added with respect to a constant amount of zinc during the bonding reaction. The results are indicated in Table 2.

TABLE 2

Effects of the Antipruritic Agent of the Present Invention on Itching Caused by Bradykinin (n = 5)

| Amino Acid | Conc. | Zinc | Conc. | Itching Activity (%) |
| --- | --- | --- | --- | --- |
| Vehicle control | — | — | — | 100.0 |
| Control | — | Zinc sulfate | $1 \times 10^{-2}$ M | 98.0 |
| Glycine | $0.5 \times 10^{-2}$ M | Zinc sulfate | $1 \times 10^{-2}$ M | 96.7 |
| Glycine | $1.0 \times 10^{-2}$ M | Zinc sulfate | $1 \times 10^{-2}$ M | 94.0 |
| Glycine | $1.5 \times 10^{-2}$ M | Zinc sulfate | $1 \times 10^{-2}$ M | 93.5 |
| Glycine | $2.0 \times 10^{-2}$ M | Zinc sulfate | $1 \times 10^{-2}$ M | 68.3 |
| Glycine | $4.0 \times 10^{-2}$ M | Zinc sulfate | $1 \times 10^{-2}$ M | 71.1 |
| Tryptophan | $0.5 \times 10^{-2}$ M | Zinc sulfate | $1 \times 10^{-2}$ M | 96.8 |
| Tryptophan | $1.0 \times 10^{-2}$ M | Zinc sulfate | $1 \times 10^{-2}$ M | 95.7 |
| Tryptophan | $1.5 \times 10^{-2}$ M | Zinc sulfate | $1 \times 10^{-2}$ M | 95.0 |
| Tryptophan | $2.0 \times 10^{-2}$ M | Zinc sulfate | $1 \times 10^{-2}$ M | 67.9 |
| Tryptophan | $4.0 \times 10^{-2}$ M | Zinc sulfate | $1 \times 10^{-2}$ M | 69.0 |
| Glutamic acid | $0.5 \times 10^{-2}$ M | Zinc sulfate | $1 \times 10^{-2}$ M | 95.7 |
| Glutamic acid | $1.0 \times 10^{-2}$ M | Zinc sulfate | $1 \times 10^{-2}$ M | 92.1 |
| Glutamic acid | $1.5 \times 10^{-2}$ M | Zinc sulfate | $1 \times 10^{-2}$ M | 91.1 |
| Glutamic acid | $2.0 \times 10^{-2}$ M | Zinc sulfate | $1 \times 10^{-2}$ M | 61.8 |
| Glutamic acid | $4.0 \times 10^{-2}$ M | Zinc sulfate | $1 \times 10^{-2}$ M | 75.5 |

As is clear from Table 2 above, the zinc-amino acid complex demonstrates favorable antipruritic effects at a mole ratio of 1:2, but the antipruritic effects per unit amount of zinc decrease if the amount of zinc is increased beyond that ratio. Similarly, the antipruritic effects per unit amount of zinc do not improve when the amount of amino acid is also increased beyond that ratio.

Thus, it is suggested that zinc and amino acid form a special bound form at a mole ratio of 1:2 that demonstrates superior antipruritic effects.

This is believed to be probably due to the zinc and amino acid forming a complex in the ratio of 1:2.

(2) Antipruritic Effects Against Itching Induced by Kallikrein in Prurigenic Animals Kallikrein is another known physiological prurigenic substance which causes itching that cannot be suppressed with anti-histamines (International Journal of Dermatology, Vol. 14, pp. 456–484, 1975).

As such, prurigenic animals in which itching cannot be suppressed with anti-histamines were prepared by intracutaneously administering kallikrein to guinea pigs, in order to confirm the antipruritic effects of the antipruritic agent according to the present invention.

Furthermore, the evaluation method used was the same as that previously described.

The hair of the right flanks of healthy male guinea pigs (body weight: 450–600 g) was shaven using an electric shaver on the previous day, and thereafter, the animals were grouped into groups of five animals each. Each of the groups were intracutaneously administered with 25 units/0.05 ml of kallikrein into the right flank. After five minutes had elapsed, an externally applied vehicle was applied to one of the groups (control group). For the other groups, 0.1 ml of each mixed compound of zinc and amino acid at each concentration was externally applied to the site of intracutaneous administration of kallikrein. The itching behavior was then observed for 20 minutes, to determine the itching activity score.

The test was thus carried out regarding the type of amino acid and antipruritic effects, based on the evaluation method described above. The results are indicated in Table 3.

TABLE 3

Effects of the Antipruritic Agent of the Present Invention on Itching Caused by Kallikrein (n = 5)

| Amino Acid | Conc. | Zinc | Conc. | Itching Activity (%) |
|---|---|---|---|---|
| Vehicle control | — | — | — | 100.0 |
| Glycine | $2 \times 10^{-2}$ M | Zinc sulfate | $1 \times 10^{-2}$ M | 72.3 |
| Tryptophan | $2 \times 10^{-2}$ M | Zinc sulfate | $1 \times 10^{-2}$ M | 78.0 |
| Glutamic acid | $2 \times 10^{-2}$ M | Zinc sulfate | $1 \times 10^{-2}$ M | 67.1 |
| Histidine | $2 \times 10^{-2}$ M | Zinc sulfate | $1 \times 10^{-2}$ M | 93.3 |
| Arginine | $2 \times 10^{-2}$ M | Zinc sulfate | $1 \times 10^{-2}$ M | 98.5 |

As is clear from Table 3 above, the antipruritic effects with respect to itching caused by kallikrein are excellent in the case of acidic to neutral amino acids such as glycine and glutamic acid.

TABLE 4

Effects of the Antipruritic Agent of the Present Invention on Itching Caused by Kallikrein (n = 5)

| Amino Acid | Conc. | Zinc | Conc. | Itching Activity (%) |
|---|---|---|---|---|
| Vehicle control | — | — | — | 100.0 |
| Control | — | Zinc sulfate | $1 \times 10^{-2}$ M | 101.3 |
| Glycine | $0.25 \times 10^{-2}$ M | Zinc sulfate | $1 \times 10^{-2}$ M | 101.0 |
| Glycine | $0.5 \times 10^{-2}$ M | Zinc sulfate | $1 \times 10^{-2}$ M | 100.9 |
| Glycine | $1.0 \times 10^{-2}$ M | Zinc sulfate | $1 \times 10^{-2}$ M | 100.9 |
| Glycine | $1.5 \times 10^{-2}$ M | Zinc sulfate | $1 \times 10^{-2}$ M | 99.9 |
| Glycine | $2.0 \times 10^{-2}$ M | Zinc sulfate | $1 \times 10^{-2}$ M | 71.3 |
| Glycine | $4.0 \times 10^{-2}$ M | Zinc sulfate | $1 \times 10^{-2}$ M | 70.8 |
| Glutamic acid | $0.25 \times 10^{-2}$ M | Zinc sulfate | $1 \times 10^{-2}$ M | 99.6 |
| Glutamic acid | $0.5 \times 10^{-2}$ M | Zinc sulfate | $1 \times 10^{-2}$ M | 99.0 |
| Glutamic acid | $1.0 \times 10^{-2}$ M | Zinc sulfate | $1 \times 10^{-2}$ M | 98.8 |
| Glutamic acid | $1.5 \times 10^{-2}$ M | Zinc sulfate | $1 \times 10^{-2}$ M | 98.1 |
| Glutamic acid | $2.0 \times 10^{-2}$ M | Zinc sulfate | $1 \times 10^{-2}$ M | 67.5 |
| Glutamic acid | $4.0 \times 10^{-2}$ M | Zinc sulfate | $1 \times 10^{-2}$ M | 72.4 |

According to Table 4, excellent effects against itching caused by kallikrein were also observed for bound forms having a zinc to amino acid ratio of 1:2.

As indicated above, it was confirmed that the antipruritic agent of the present invention can be a new antipruritic agent having an effect against itching that cannot be suppressed with conventional anti-histamines and so on.

(3) Effects Due to Formation of a Complex

Next, the inventors of the present invention compiled the following experimental system, in order to confirm whether the antipruritic effects of the present invention were due to the blending ratio of the zinc and amino acid, or due to the formation of a bound form (complex).

In Table 5 shown below, in the case of an amino acid alone, the amino acid was dissolved to a concentration of $1 \times 10^{-2}$M. In the case of the zinc sulfate-amino acid mixture groups, the zinc sulfate was dissolved to a concentration of $1 \times 10^{-2}$M and the amino acid was dissolved to a concentration of $2 \times 10^{-2}$M. In the case of a zinc-amino acid complex, the complex was dissolved to a concentration of $1 \times 10^{-2}$M. In each case, water was used for the solvent. These solutions were then used as the test samples.

The bound substances (precipitates) formed in the above-mentioned Examples 1–9 are considered to be complexes, and stirring is required over an extended period of time in order to obtain the bound substances. Consequently, even if the zinc sulfate and amino acid were simply dissolved in solvent (zinc sulfate-amino acid mixture groups), the bound form (complex) essentially would not be formed.

TABLE 5 n = 5

| | Itching Activity | |
|---|---|---|
| | Bradykinin | Kallikrein |
| Vehicle control group | 100 | 100 |
| Glutamic acid alone | 101 | 102 |
| Zinc sulfate-glutamic acid mixture group | 87 | 90 |
| Zinc-glutamic acid complex | 65 | 67 |
| Vehicle control group | 100 | 100 |
| Aspartic acid alone | 101 | 101 |
| Zinc sulfate-aspartic acid mixture group | 91 | 91 |
| Zinc-aspartic acid complex | 70 | 69 |
| Vehicle control group | 100 | 100 |
| Glycine alone | 98 | 99 |

TABLE 5-continued

|  | n = 5 Itching Activity | |
| --- | --- | --- |
|  | Bradykinin | Kallikrein |
| Zinc sulfate-glycine mixture group | 88 | 92 |
| Zinc-glycine complex | 73 | 75 |

According to Table 5 above, the antipruritic agent according to the present invention possesses remarkable effects as a complex, and in addition, it is clear that it does not demonstrate antipruritic effects simply as a result of the coexistence of zinc and amino acid.

The following provides an explanation of the antipruritic composition which uses the antipruritic agent according to the present invention.

First, the composition of an external use antipruritic composition into which is blended the antipruritic agent according to the present invention, together with its pharmacological effects, are indicated in Table 6 below. Note, the blended amounts are indicated in wt %.

TABLE 6

|  |  | Example 10 | Example 11 | Comp. Example 1 | n = 5 Comp. Example 2 |
| --- | --- | --- | --- | --- | --- |
| (1) | Zinc-glycine complex*1 | 0.23 | 0.23 | — | — |
| (2) | Zinc sulfate*2 | — | — | 0.27 | 0.27 |
| (3) | Glycine | — | 5.0 | — | 0.08 |
| (4) | Glycerol |  |  | 20.0 |  |
| (5) | Propylene glycol |  |  | 10.0 |  |
| (6) | Ethyl alcohol |  |  | 5.0 |  |
| (7) | Hydroxypropyl cellulose |  |  | 1.0 |  |
| (8) | Methylparabenzene |  |  | 0.05 |  |
| (9) | Purified water |  |  | Balance |  |
|  |  |  | Total 100.0% |  |  |
| Itching Activity |  | Example 10 | Example 11 | Comp. Example 1 | Comp. Example 2 |
| Bradykinin-induced itching |  | 64 | 65 | 97 | 86 |
| Kallikrein-induced itching |  | 66 | 68 | 94 | 89 |

*1Monohydrate
*2Hexahydrate (each equivalent to roughly $1 \times 10^{-2}$ M)

Preparation Process

Ingredients (1) and (8) were added to ingredients (4) and (6), followed by heating to 40°–50° C. and stirring until dissolved. On the other hand, ingredient (5) was wetted in advance with ingredient (7) followed by the addition of ingredients (2), (3) and (9). After stirring until dissolved, the compound dissolved above was added gradually and stirred to obtain the desired preparation.

This antipruritic composition was stable even after long-term storage at temperatures over a range of −5 to 40° C.

According to Table 6 above, the antipruritic compositions according to Example 10 and Example 11 possess a superior antipruritic activity. In addition, as is clear from Example 11, the presence of excess amino acid does not have an effect on antipruritic activity.

On the other hand, as described above, the zinc-amino acid complex is first formed by stirring for an extended time in the presence of both zinc and amino acid. As indicated in Comparative Example 2, it is believed that simply blending zinc sulfate and glycine into the compound essentially does not result in the formation of the bound substance (complex), due in part to the relationship thereof with other ingredients.

As a result, it was determined that, in order for the composition to sufficiently demonstrate antipruritic effects, preferably the zinc-amino acid complex is formed in advance, after which said zinc-amino acid complex is added to each of the other ingredients.

Example 12

External Use Antipruritic Agent

| (1) Zinc-serine complex | 1.0 wt % |
| --- | --- |
| (2) Isopropyl alcohol | 25.0 wt % |
| (3) Polyethylene glycol 300 | 20.0 wt % |
| (4) Glycerol | 20.0 wt % |
| (5) Phosphate buffer | q.s. |
| (6) Purified water | Balance |

Manufacturing Process

After adding ingredient (1) to ingredients (2) and (4), heating to a temperature of 40°–50° C. and stirring until dissolved, ingredient (3) was added followed by stirring and mixing. On the other hand, a solution resulting from dissolving ingredient (5) in ingredient (6) by stirring was added to the previously prepared liquid, followed by stirring, to obtain a stable preparation of pH=5.6.

This antipruritic was stable even when stored for an extended time at −5 to 40° C. Moreover, the antipruritic effects were extremely high, as indicated in the abovementioned test of antipruritic properties.

Example 13

External Use Antipruritic Agent

| (1) Zinc-cysteine complex | 3.0 wt % |
| --- | --- |
| (2) Glycerol | 40.0 wt % |
| (3) Ethyl alcohol | 25.0 wt % |
| (4) 1,3-butylene glycol | 10.0 wt % |
| (5) Isopropyl adipate | 1.0 wt % |
| (6) Hydroxymethyl cellulose | 0.3 wt % |
| (7) Purified water | Balance |

Preparation Process

Ingredient (1) was added to ingredients (2) and (3), and after heating to a temperature of 40°–50° C. and stirring until dissolved, ingredients (4) and (5) were sequentially added, followed by stirring and mixing. On the other hand, after dissolving ingredient (6) in ingredient (7), the composition prepared above was added gradually, and sufficiently stirred to obtain a stable preparation of pH=5.50.

This antipruritic agent was stable even when stored for an extended time at −5 to 40° C. Moreover, the antipruritic effects were extremely high, as indicated in the above-mentioned test of antipruritic properties.

Example 14

External Use Antipruritic Agent

| (1) Zinc-leucine complex | 5.0 wt % |
| --- | --- |
| (2) Glycerol | 45.0 wt % |
| (3) Ethyl alcohol | 30.0 wt % |
| (4) Dipropylene glycol | 10.0 wt % |
| (5) Diethyl adipate | 1.0 wt % |

(6) Purified water     Balance

Preparation Process

To ingredient (1) was added ingredients (2) and (4), and after heating to a temperature of 40°–50° C. and stirring until dissolved, ingredients (4), (5) and (6) were added sequentially, followed by stirring, to obtain a stable preparation of pH=5.2.

This antipruritic agent was stable even when stored for an extended time at -5 to 40° C. Moreover, the antipruritic effects were extremely high, as indicated in the above-mentioned test of antipruritic properties.

Example 15

Sunburn Cream

| | | |
|---|---|---|
| (1) | Stearic acid | 2.0 wt % |
| (2) | Cetanol | 5.0 wt % |
| (3) | Hydrogenated oil | 5.0 wt % |
| (4) | Silicone KF96A-6 | 5.0 wt % |
| (5) | Squalane | 10.0 wt % |
| (6) | (POE)$_{40}$ stearyl ester | 2.0 wt % |
| (7) | Glyceryl monostearate | 3.0 wt % |
| (8) | Glycerol | 10.0 wt % |
| (9) | Zinc-methionine complex | 0.5 wt % |
| (10) | Antioxidant, preservative and perfume | q.s. |
| (11) | Purified water | Balance |

Preparation Process

Ingredients (1) through (7) and ingredient (10) were heated to dissolve at 70° C. to prepare the oil phase.

On the other hand, ingredient (9) was added to ingredients (3) and (11). After heating and stirring until dissolved, the oil phase was gradually added, followed by processing with a homogenizer and cooling.

This suntan cream was stable when stored for an extended time at −5 to 40° C.

Example 16

Milky Lotion

| | | |
|---|---|---|
| (1) | Cetanol | 0.5 wt % |
| (2) | Hydrogenated | 1.0 wt % |
| (3) | Stearic acid | 1.0 wt % |
| (4) | Squalane | 3.0 wt % |
| (5) | (POE)$_{20}$ mol sorbitan monolaurate | 1.0 wt % |
| (6) | Glyceryl monostearate | 1.0 wt % |
| (7) | Ethyl paraben | 0.15 wt % |
| (8) | Perfume | 0.2 wt % |
| (9) | Glycerol | 10.0 wt % |
| (10) | Dipropylene glycol | 5.0 wt % |
| (11) | Zinc-tyrosine complex | 1.0 wt % |
| (12) | Carboxyvinyl polymer 105 | 0.3 wt % |
| (13) | Triethanol amine | 1.0 wt % |
| (14) | Purified water | Balance |

Preparation Process

Ingredients (1) through (8) were heated at 70° C. and stirred until dissolved, to prepare the oil phase. In addition, ingredient (11) was dissolved in ingredients (9) and (10) and a portion of ingredient (14), to prepare the zinc-tyrosine complex phase. On the other hand, ingredient (13) was dissolved in the majority of ingredient (14) and heated to 70° C., to prepare the aqueous phase; this was then gradually added to the oil phase, followed by emulsion. After adding that in which ingredient (12) was dissolved in a portion of ingredient (14), the zinc-tyrosine complex phase was added, followed by processing with a homogenizer, stirring, and cooling to obtain the milky lotion.

This milky lotion was stable even when stored for an extended time at −5 to 40° C.

Example 17

Skin Wash

| | | |
|---|---|---|
| (1) | Glycerol | 5.0 wt % |
| (2) | Denatured ethyl alcohol | 15.0 wt % |
| (3) | (POE)$_{60}$ hydrogenated castor oil | 1.0 wt % |
| (4) | Zinc-tryptophan complex | 0.3 wt % |
| (5) | Perfume | q.s. |
| (6) | Methyl paraben | 0.2 wt % |
| (7) | Allantoin | 0.1 wt % |
| (8) | Purified water | Balance |

Preparation Process

Ingredients (1) through (6) were stirred until dissolved, at room temperature, to prepare the alcohol phase. In addition, after dissolving ingredient (7) in ingredient (8), the alcohol phase was gradually added while stirring, to form a uniform solution to obtain a skin wash.

This skin wash was stable when stored for an extended time at −5 to 40° C. and moreover, possessed skin conditioning effects.

Example 18

Sunburn Ointment

| | | |
|---|---|---|
| (1) | Zinc-glutamic acid complex | 2.5 wt % |
| (2) | Glycerol | 35.0 wt % |
| (3) | Polyethylene glycol (PEG-400) | 25.0 wt % |
| (4) | Polyethylene glycol (PEG-6000) | 5.0 wt % |
| (5) | Hydrogenated oil | 12.0 wt % |
| (6) | Stearic acid | 2.0 wt % |
| (7) | Isopropyl palmitate | 2.0 wt % |
| (8) | Glyceryl monostearate | 3.0 wt % |
| (9) | Methyl paraben | 0.2 wt % |
| (10) | Potassium hydroxide | 0.1 wt % |
| (11) | Purified water | 13.2 wt % |

Preparation Process

Ingredients (1) through (4) and a portion of ingredient (11) were added and stirred at 70° C. until dissolved, to prepare the zinc-glutamic acid complex phase. On the other hand, ingredients (5) through (9) were heated to 70° C. to prepare the oil phase. Ingredient (10) was added to ingredient (11), followed by heating until dissolved, into which was then added the above oil phase. Finally, the previously prepared zinc-glutamic acid complex phase was added. After creating a uniform mixture with a homogenizer, the mixture was stirred and cooled to obtain the sunburn ointment.

This ointment was stable when stored for an extended time at −5 to 40° C.

Example 19

Emulsion Ointment

| | | |
|---|---|---|
| (1) | Diglycerol isostearate | 2.0 wt % |

-continued

| | | |
|---|---|---|
| (2) | Water-swelling clay mineral (hectrite)*1 | 1.5 wt % |
| (3) | Benzyldimethylstearylammonium chloride | 0.5 wt % |
| (4) | Dimethyl polysiloxane | 5.0 wt % |
| (5) | Liquid paraffin | 18.8 wt % |
| (6) | Microcrystalline wax | 2.0 wt % |
| (7) | Ethyl paraben | 0.2 wt % |
| (8) | Deionized water | 10.0 wt % |
| (9) | Glycerol | 48.0 wt % |
| (10) | Propylene glycol | 10.0 wt % |
| (11) | Zinc-histidine complex | 2.0 wt % |

Preparation Process

After sufficiently allowing ingredient (2) to swell inside ingredient (8), it was dispersed in a solution in which ingredients (9), (10) and (11) were heated and dissolved in advance, to form the aqueous phase.

On the other hand, oil-soluble ingredients (1) and (3) through (7) were mixed and dissolved at roughly 0° C. to obtain the oil phase When the above aqueous phase was gradually added while stirring the oil phase with a stirring rod, an emulsified dispersion system was obtained. This was then cooled to room temperature to obtain the desired emulsion ointment.

This emulsion ointment was stable when stored for an extended time at −5 to 40° C., and possessed skin conditioning effects.

Furthermore, the water-swelling clay mineral used 1 in this Example is a type of colloidal hydrate aluminum silicate having a three layer structure, and is generally expressed with the general formula indicated below:

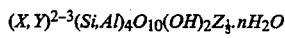

$$(X,Y)^{2-3}(Si,Al)_4O_{10}(OH)_2Z_{\frac{1}{3}} \cdot nH_2O$$

where, $X = Al, Fe_{III}, Mn_{III}, Cr_{III}$ $Y = Mg, Fe, Ni_{II}, Zn, Li$ $Z = K, Na, Ca$ More specifically, this is comprised of natural or synthetic (in this case, the (OH) group in the formula is substituted with fluorine) members of the montmorillonite group such as montmorillonite, saponite and hectrite.

Example 20

Hair Tonic

| | | |
|---|---|---|
| (1) | Denatured ethyl alcohol | 65.0 wt % |
| (2) | Propylene glycol | 5.0 wt % |
| (3) | Glycerol | 5.0 wt % |
| (4) | Zinc-arginine complex | 0.5 wt % |
| (5) | Perfume | q.s. |
| (6) | (POE)$_{60}$ hydrogenated castor oil | 1.0 wt % |
| (7) | Hinokitiol | 0.01 wt % |
| (8) | Vitamin E acetate | 0.1 wt % |
| (9) | Purified water | Balance |

Manufacturing Process

After heating and dissolving ingredient (4) in ingredients (1), (2) and (3), ingredients (5), (6) and (7) were added followed by stirring until dissolved. Moreover, ingredient (9) was added gradually while stirring to obtain the hair tonic.

This hair tonic was stable when stored for an extended time at −5 to 40° C.

Example 21

Tablet 100 mg of lactose, 30 mg of cornstarch, 80 mg of talc and 2 mg of magnesium stearate were added and mixed with 100 mg of zinc-lysine complex and formed into tablets.

In the case of an enteric coated preparation, the above-mentioned tablet was coated with an enteric coating of hydroxypropylmethyl cellulose phthalate to obtain the enteric coated tablet.

This tablet was stable when stored for an extended time at −5 to 40° C.

Example 22

Capsule 150 mg of lactose, 100 mg of cornstarch and 1 mg of light-gravity silicic anhydride were added and mixed with 50 mg of zinc-glysine complex and filled into a No. 2 gelatin hard capsule. In the case of an enteric coated capsule, the above-mentioned capsule was coated with an enteric coating of hydroxypropylmethyl cellulose phthalate to obtain the enteric coated capsule. This capsule was stable when stored for an extended time at −5 to 40° C.

Example 23

Injection Preparation

Zinc-serine complex was dissolved in Japanese Pharmacopoeia physiological saline in the proportion of 10 mg of complex to 10 ml of saline. This solution was then filtered through a sterile membrane filter. After dividing the filtrate among sterilized ampules, the ampules were sealed.

This injection preparation was stable when stored for an extended time at −5 to 40° C.

Industrial Applicability

According to the antipruritic agent or antipruritic composition of the present invention containing a zinc-amino acid complex, it is able to demonstrate superior antipruritic effects even with respect to itching for which sufficient antipruritic effects were unable to be obtained with conventional antipruritic agents or antipruritic compositions.

We claim:

1. An antipruritic agent comprising a zinc-amino acid complex of a naturally occurring α-amino acid.

2. An antipruritic agent as claimed in claim 1, wherein the bonding mole ratio of zinc-amino acid of the above-mentioned zinc-amino acid complex is 1:2.

3. An antipruritic agent as claimed in claim 1, wherein the α-amino acid is at least one compound selected from the group consisting of acidic α-amino acids and neutral α-amino acids.

4. An antipruritic compositions comprising the antipruritic agent described in claim 1 at a concentration of $2.6 \times 10^{-3}$ to $2.6 \times 10^{-1}$ M, and a pharmacologically acceptable carrier.

5. An antipruritic agent as claimed in claim 2, wherein the α-amino acid is at least one compound selected from the group consisting of acidic α-amino acids and neutral α-amino acids.

6. An antipruritic composition comprising the antipruritic agent described in claim 2 at a concentration of $2.6 \times 10^{-3}$ to $2.6 \times 10^{-1}$M, and a pharmacologically acceptable carrier.

7. An antipruritic composition comprising the antipruritic agent described in claim 3 at a concentration of $2.6 \times 10^{-3}$ to $2.6 \times 10^{-1}$M, and a pharmacologically acceptable carrier.

8. An antipruritic composition comprising the antipruritic agent described in claim 5 at a concentration of $2.6 \times 10^{-3}$ to $2.6 \times 10^{-1}$ M, and a pharmacologically acceptable carrier.

9. An antipruritic agent comprising a zinc-glutamic acid complex having the following formula:

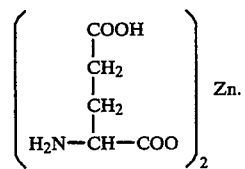

* * * * *